(12) United States Patent  
Yasuhara

(10) Patent No.: US 8,253,101 B2
(45) Date of Patent: Aug. 28, 2012

(54) METHOD AND SYSTEM FOR ACQUISITION OF CONFOCAL STEM IMAGES

(75) Inventor: Akira Yasuhara, Tokyo (JP)

(73) Assignee: JEOL Ltd., Tokyo (JP)

( * ) Notice: Subject to any disclaimer, the term of this patent is extended or adjusted under 35 U.S.C. 154(b) by 181 days.

(21) Appl. No.: 12/884,336

(22) Filed: Sep. 17, 2010

(65) Prior Publication Data

US 2011/0062326 A1 Mar. 17, 2011

(30) Foreign Application Priority Data

Sep. 17, 2009 (JP) ................................. 2009-215458

(51) Int. Cl.
*G01N 23/00* (2006.01)
(52) U.S. Cl. ......... 250/311; 250/306; 250/307; 250/310
(58) Field of Classification Search .................. 250/306, 250/307, 310, 311
See application file for complete search history.

(56) References Cited

U.S. PATENT DOCUMENTS

| 6,548,810 | B2 | 4/2003 | Zaluzec |
| 7,109,485 | B2 * | 9/2006 | Takane et al. ................. 250/310 |
| 2009/0078868 | A1 | 3/2009 | de Jonge |

FOREIGN PATENT DOCUMENTS

| JP | 2008270056 A | 11/2008 |
| JP | 2009236764 A | 10/2009 |

* cited by examiner

*Primary Examiner* — Michael Maskell
(74) *Attorney, Agent, or Firm* — The Webb Law Firm

(57) ABSTRACT

Method and system to obtain confocal STEM images. Arithmetic and control device extracts diffraction images respectively corresponding to successive pixel positions from the images stored in the memory, selects and corrects center positions of the extracted diffraction images, creates an image set having diffraction information in which the center positions of the diffraction images have been corrected and aligned, selects only innermost portions of the diffraction images of the created image set, and reproduces STEM images from the diffraction images, thus obtaining a confocal STEM image.

2 Claims, 6 Drawing Sheets

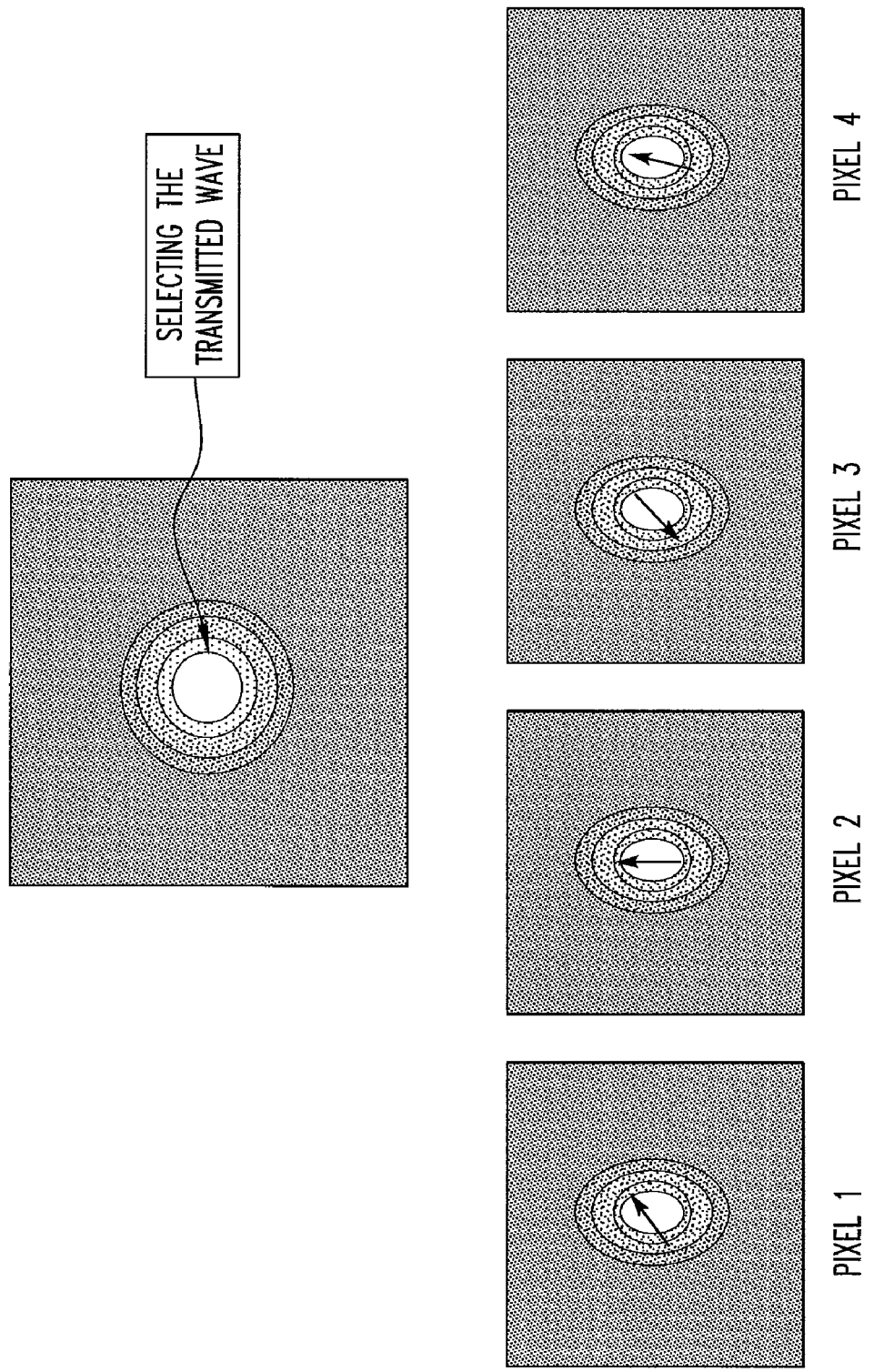

METHOD AND SYSTEM FOR ACQUISITION OF CONFOCAL STEM IMAGES

BACKGROUND OF THE INVENTION

1. Field of the Invention

The present invention relates to a method and system for acquisition of confocal STEM (scanning transmission electron microscope) images. More particularly, the invention relates to a simplified system for acquiring confocal STEM images. The invention also relates to a method using this simplified system.

2. Description of Related Art

An electron beam extracted from an electron gun is accelerated by an acceleration tube and made to hit a thin-film sample. When passing through the thin-film sample, the beam interacts with the sample. As a result, the orbit or phase may be varied or the beam may interact with the atoms in the sample, thus producing energy loss.

In confocal TEM (transmission electron microscopy), impinging electrons emitted from an electron gun are focused onto a sample by condenser lenses. Electrons transmitted through the sample are again focused at the position of an aperture by an imaging lens, the aperture being located on the upper surface of a detector that lies under the sample. The aperture permits only a part of the central portion of the focused electron beam on the sample to pass through, and the central portion is detected by a detector.

FIG. 6 shows one example of the prior art instrument. The instrument has an electron gun 1 and a condenser lens 2 for focusing the extracted electrons. A sample 10 is placed behind the condenser lens 2. A piezo actuator 3 moves the sample 10 in a direction perpendicular to the optical axis. An imaging lens 4 brings a signal including electrons transmitted through the sample 10 into focus. A pinhole-type aperture 5 is located at a focal point lying under the imaging lens 4. An image signal transmitted through the aperture 5 is detected by a detector 6. The sample is moved in three dimensions by a goniometer 9.

The instrument further includes a control imaging system personal computer (PC) 7 and an electron microscope system personal computer (PC) 8. The control imaging system PC 7 receives the output signal from the detector 6 and supplies a control signal to the piezo actuator 3. The microscope system PC 8 controls the condenser lens 2, the goniometer 9, and the imaging lens 4. The operation of the instrument constructed in this way is next described.

The electron beam emanating from the electron gun 1 is finely focused onto the sample 10 by the condenser lens 2 while being scanned in two dimensions. A signal such as electrons transmitted through the sample 10 is made to impinge on the detector 6 through the imaging lens 4 and aperture 5. If the aperture 5 is made of a pinhole-type aperture, transmitted electrons coming only from the focal position can be derived.

The derived, transmitted electrons are detected by the detector 6. The output signal from the detector is applied to the control imaging system PC 7 and stored in a memory (not shown). At this time, the scanning of the sample is controlled by the electron microscope system PC 8 and synchronized with the output signal from the detector 6. Thus, a confocal image can be obtained.

In this prior art instrument, the optical system is fixed, and only the sample 10 is scanned with the piezo actuator 3. As a result, the imaging system does not need to have any scanning system.

Another known instrument of this type can obtain information in the depth direction of the sample by applying image computations of annular dark-field scanning transmission electron microscopy (ADF-STEM) to confocal scanning transmission electron microscopy (STEM) and deriving confocal STEM images.

A further known instrument of this type is described, for example, in JP-A-2008-84643 (paragraphs 0013-0027; FIGS. 1-3). In particular, the intensity of an electron beam transmitted through a sample is measured while making the focal position of the electron beam vary in the depth direction of the sample. The absorption of the electron beam into the sample and the distribution of scattering in the depth direction are measured.

Furthermore, a technique is known which uses a nanoactuator to permit a sample stage holding a sample thereon to be moved adjustably in the Z-axis direction (along the optical axis of an electron beam) and in the X-axis and Y-axis directions perpendicular to the Z-axis direction (see, for example, JP-A-2008-270056 (paragraphs 0019-0023; FIGS. 4-6 and 12-13).

Where the scanning transmission electron microscope (STEM) shown in FIG. 6 is used and a confocal STEM image should be obtained, a special pinhole-type aperture needs to be placed ahead of the detector 6. The beam is scanned over the sample such that it can pass through the pinhole to obtain a confocal image and that mixing of other signals is prevented. In addition, the imaging system is required to have a scanner for scanning the beam. In this case, it is essential that the scanning of the imaging system be done interlockingly with the scanning over the sample. It is difficult for any ordinary instrument to achieve this requirement. Furthermore, it is difficult to control.

In order to moderate the above-described problem, in the instrument of FIG. 6, the scanning of the electron beam is halted to cease the beam over the sample in the spot mode. Under this condition, the sample is scanned, thus dispensing with scanning of the imaging system. However, this instrument is also required to scan the sample on a sub-Angstrom scale. This creates the problem of sample drift. In addition, as the sample is moved in the x- and y-directions, the position shifts in the z-direction. It is difficult to control because the x- and y-directions are normally created by cooperation between the x- and y-directions of a goniometer.

SUMMARY OF THE INVENTION

The present invention has been developed in view of these problems. The objects of the invention are as follows.

1) In the present invention, diffraction images are recorded with a CCD camera in synchronism with scanning.

2) Scanning of the imaging system is dispensed with by obtaining image data from diffraction patterns (represented by an imaging system signal) recorded in the CCD camera, then detecting the center positions of the diffraction images from the image data, and making positional corrections.

3) The pinhole-type aperture positioned ahead of the detector is dispensed with by extracting central portions of the diffraction patterns from the positionally corrected scanned images including the diffraction patterns, taking image data only from the central portions, and reproducing the images.

4) Confocal STEM images can be obtained with ordinary equipment without using special devices.

In this way, the present invention is intended to provide simplified method and apparatus for acquiring confocal STEM images.

In order to solve the foregoing problems, the present invention is configured as follows.

(1) A first embodiment of the present invention provides a method of obtaining a confocal STEM image, the method starting with scanning a sample with an electron beam in two dimensions. A signal emanating from the sample is detected by a detector. The signal detected by the detector is converted into digital data and stored as image data into a memory. Diffraction images respectively corresponding to successive pixel positions are extracted from the images stored in the memory. The center positions of the extracted diffraction images corresponding to the pixel positions are selected and corrected. An image set having diffraction information in which the center positions of the diffraction images respectively corresponding to the pixel positions have been corrected and aligned is created. Only innermost portions of the diffraction images of the created image set which correspond to the successive pixel positions are selected. STEM images are reproduced from the diffraction images. Thus, a confocal STEM image is obtained.

(2) A second embodiment of the invention provides a system for obtaining a confocal STEM image, the system having a detector for detecting a signal emanating from a sample when it is scanned in two dimensions with an electron beam, a memory for storing image data obtained by converting the signal detected by the detector into digital data, and arithmetic and control means connected with the detector and the memory. The arithmetic and control means controls the detector, reads images from the memory, and performs given computational processing. The arithmetic and control means extracts diffraction images respectively corresponding to successive pixel positions from the images stored in the memory, selects and corrects the center positions of the extracted diffraction images corresponding to the pixel positions, creates an image set having diffraction information in which the center positions of the diffraction images have been corrected and aligned, selects only innermost portions of the diffraction images of the created image set, and reproduces STEM images from the diffraction images, thus obtaining a confocal STEM image.

The present invention yields the following advantages.

(1) The method according to the first embodiment of the invention makes it possible to perform confocal STEM imaging with an ordinary scanning transmission electron microscope (STEM) without using any special detector aperture or imaging system scanning that interlocks with illumination system scanning.

(2) The system according to the second embodiment of the invention makes it possible to perform confocal STEM imaging with an ordinary scanning transmission electron microscope (STEM) without using any special detector aperture or imaging system scanning that interlocks with illumination system scanning.

Other features and advantages of the present invention will become apparent from the following more detailed description, taken in conjunction with the accompanying drawings, which illustrate, by way of example, the principles of the invention.

BRIEF DESCRIPTION OF THE DRAWING(S)

FIG. 3 illustrates the manner in which the center positions of diffraction images are selected and corrected;

DESCRIPTION OF THE PREFERRED EMBODIMENT(S)

Figure 1:
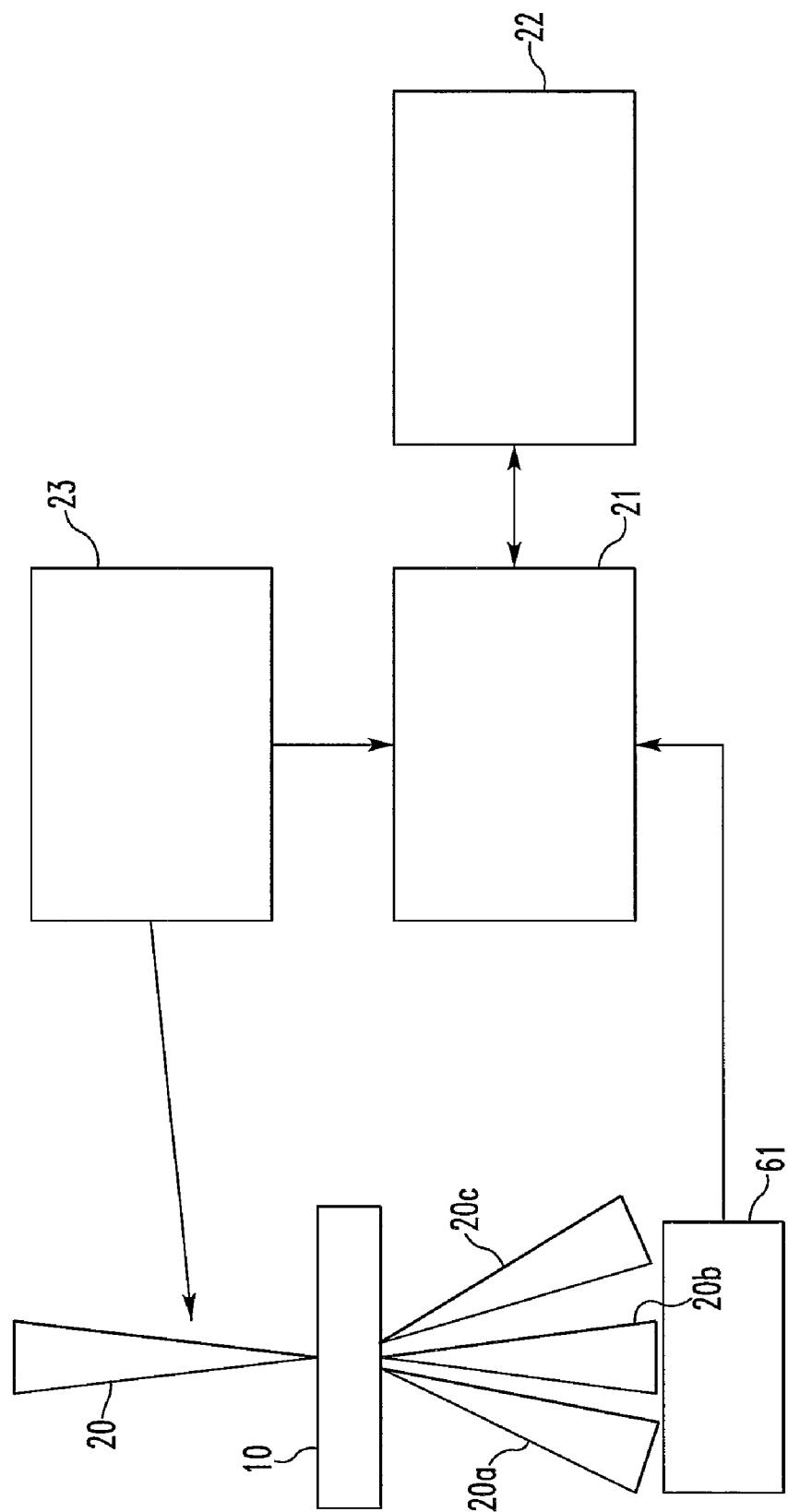
FIG. 1 is a block diagram of a confocal STEM imaging system according to the present invention, illustrating its principle.
Figure 6:
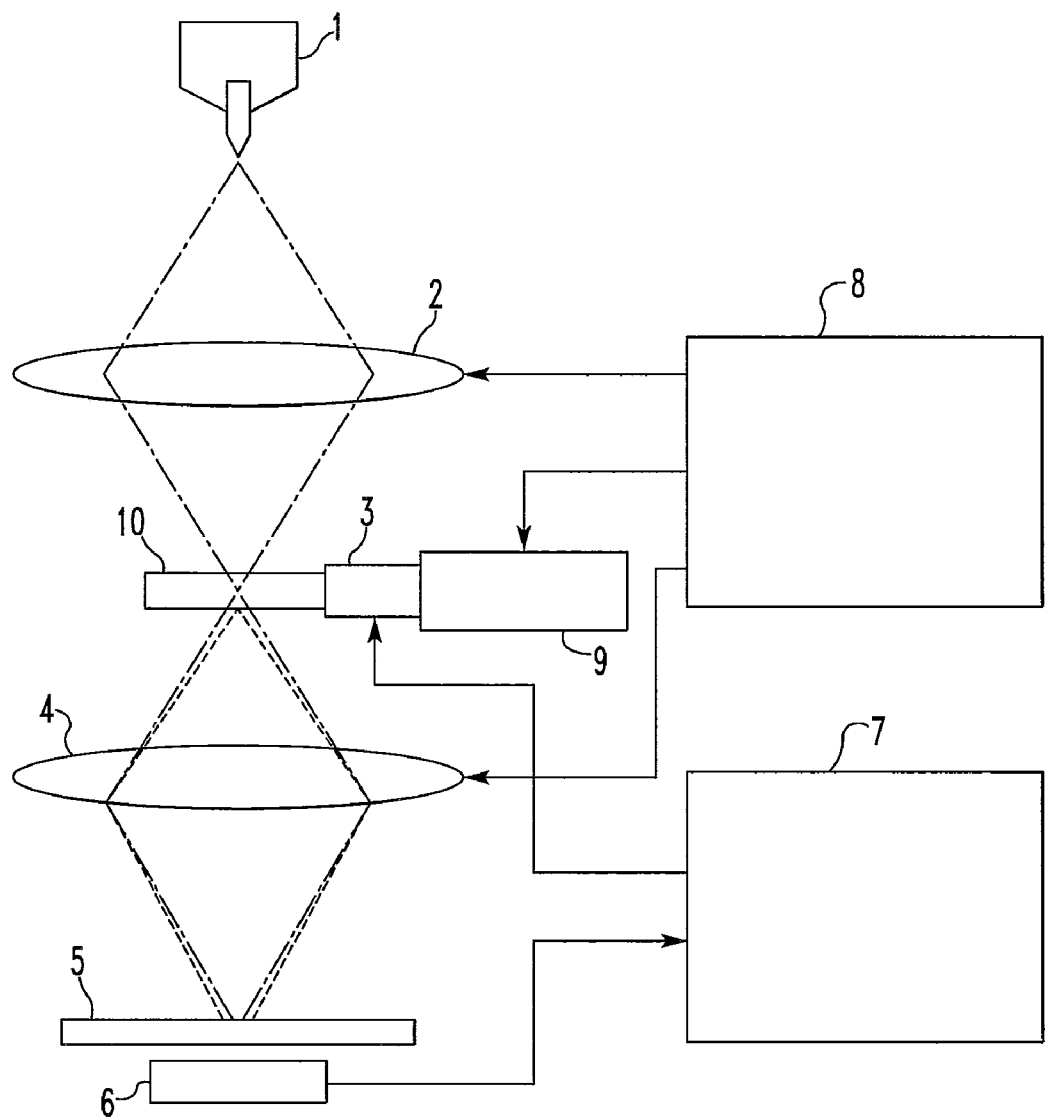
FIG. 6 is a block diagram of a prior art confocal STEM imaging system.

Embodiments of the present invention are hereinafter described in detail with reference to the drawings. FIG. 1 is a block diagram of a confocal imaging system according to the present invention, illustrating its principle. In FIGS. 1 and 6, like components are indicated by like reference numerals. An electron probe 20 is focused onto a sample 10. The probe 20 is scanned over the sample 10 according to an external scanning control signal. The probe 20 impinging on the sample 10 interacts with the sample 10. As a result, the probe exits in directions indicated by 20a-20c.

A CCD camera 61 detects a transmission electron image. The output signal from the camera 61 is converted into an electrical signal and then into image data. A personal computer (PC) 21 for controlling the CCD camera 61 acts as arithmetic and control means. The computer 21 accepts the image data, converts it into digital image data, and stores it into a memory 22. The computer 21 reads image data from the memory 22 and performs given computational processing (described later).

Another personal computer (PC) 23 controlling the electron microscope supplies an electron beam scanning control signal to the illumination optical system (not shown) to scan the electron probe 20 in two dimensions over the sample. The computer 23 furnishes scanning information to the CCD camera-controlling PC 21 to synchronize the image acquisition. As can be seen from FIG. 1, the present invention dispenses with any imaging optical system. The operation of the system constructed in this way is next described.

Figure 2A:
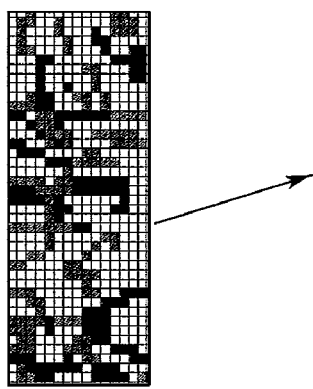
FIGS. 2A and 2B illustrate the manner in which a diffraction image corresponding to a pixel position is extracted from a scanned image.
Figure 2B:
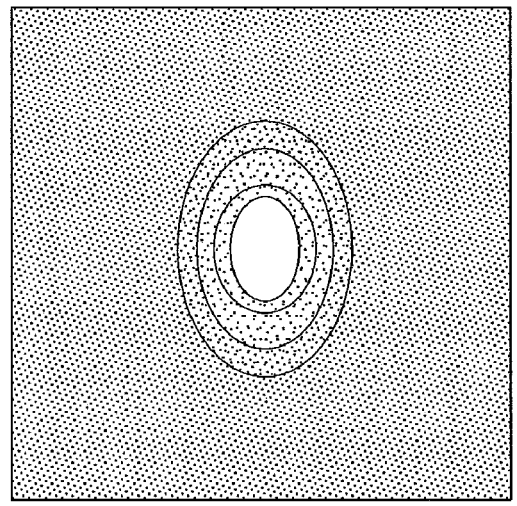

(1) FIGS. 2A and 2B illustrate the manner in which diffraction images respectively corresponding to successive pixel positions are extracted from transmission images. First, the microscope-controlling PC 23 (hereinafter abbreviated as PC2) scans the electron probe 20 over the sample 10.

(2) The electron beam 20 is scanned over the sample 10. As a result, transmitted and scattered electrons are emitted from the sample 10. The CCD camera 61 detects electrons transmitted through the sample 10, which represent a transmission image, in synchronism with the scanning and sends the resulting signal to the CCD camera-controlling PC 21 (hereinafter abbreviated as PC1). The PC 21 converts the analog image data sent in from the CCD camera 61 into digital image data by an A/D converter (not shown) and stores the data into the memory 22.

(3) Then, PC1 reads images from the memory 22 and extracts diffraction images respectively corresponding to successive pixel positions from the images read out. FIGS. 2A and 2B illustrate the manner in which the diffraction images respectively corresponding to successive pixel positions are extracted from the images read out. FIG. 2A indicates a scanned image, while FIG. 2B indicates a diffraction image. A diffraction image for each pixel position surrounded by the rectangular region of FIG. 2A is extracted. The scanned image and the diffraction image form a pair and so it is easy to extract the diffraction images from the scanned images (i.e., to convert the scanned images into the diffraction images) for successive pixel positions using the existing technique.

(4) PC1 selects the center position (representing the transmitted wave) of each diffraction image extracted in step (3) above and makes a drift correction. FIG. 3 illustrates the manner in which the center position of each diffraction image is selected and corrected. The transmitted wave near the center is selected, and the center position (representing the transmitted wave) of the selected diffraction image is corrected. In FIG. 3, the center positions of the diffraction images respectively corresponding to successive pixel positions (such as pixel positions 1-4) are shifted in the directions of the arrows, and each center position is corrected. This method is accomplished by correcting the center positions instead of corrections being made by the scanner of the imaging system.

When the sample is scanned, the diffraction patterns shift on the photosensitive surface of the CCD camera 61. It is necessary to correct the motion such that the pattern is brought back to center. This is equivalent to scanning the projection system and holding it at the pinhole. The center position is corrected by calculating the magnitude of the deviation, for example, using an intercorrelation function and correcting the center position of each diffraction image by an amount equal to the calculated amount of deviation.

Figures 4A, 4B:
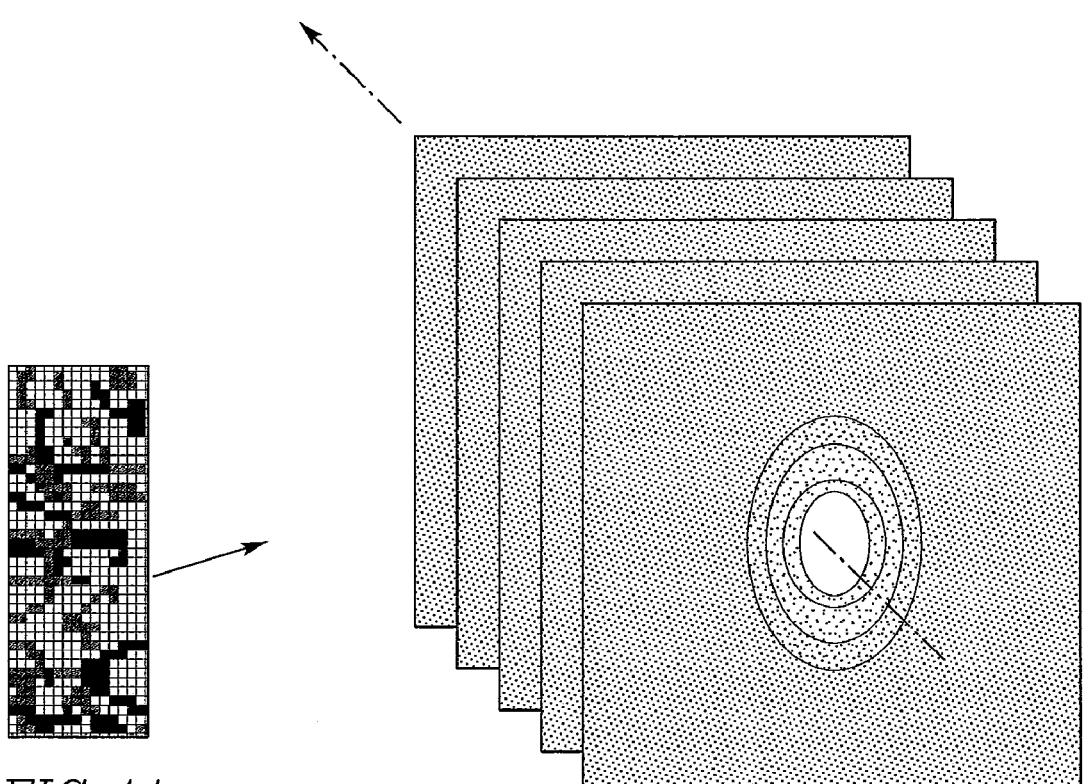
FIGS. 4A and 4B illustrate an image set having diffraction information in which the center positions of the diffraction images respectively corresponding to successive pixel positions have been aligned.

(5) PC1 creates an image set having diffraction information in which the center positions (representing the transmitted wave) of the diffraction images respectively corresponding to successive pixel positions have been aligned. This image set is shown in FIG. 4B, along with a STEM image in FIG. 4A. FIG. 4A shows a STEM image where the center of a diffraction image was present. STEM images respectively corresponding to successive pixel positions contain their respective diffraction patterns. FIG. 4B shows the image set composed of the diffraction images which correspond to the successive pixel positions and which were positionally corrected in step (4) above.

Figure 5A:
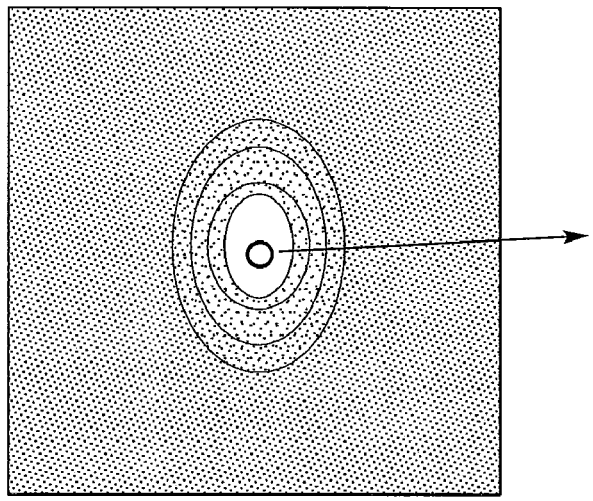
FIGS. 5A and 5B illustrate the manner in which a confocal STEM image is created.
Figure 5B:
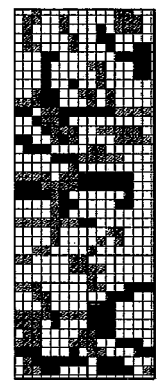

(6) PC1 selects innermost portions of the diffraction images forming the image set and obtains a confocal STEM image. FIGS. 5A and 5B illustrate the manner in which the confocal STEM image is created. FIG. 5A shows a diffraction image corresponding to one pixel position, and FIG. 5B shows a confocal STEM image obtained by selecting only an innermost portion of the diffraction image and performing a conversion. Only the innermost portion is selected because a precise confocal STEM image should be derived in the same way as a confocal STEM image acquired by a pinhole in the prior art system.

As described in detail so far, according to the present invention, a confocal STEM image can be obtained with an ordinary scanning transmission electron microscope (STEM) without using any special detection aperture and without using an illumination system scanner or an imaging system scanner.

Having thus described my invention with the detail and particularity required by the Patent Laws, what is desired protected by Letters Patent is set forth in the following claims.

The invention claimed is:

1. A method of obtaining a confocal STEM image, comprising the steps of:
    scanning an electron beam over a sample in two dimensions;
    detecting a diffraction image signal emanating from the sample by a detector;
    converting the diffraction image signal detected by the detector into digital data;
    storing the digital data as image data into a memory;
    extracting diffraction images respectively corresponding to successive pixel positions from images stored in the memory;
    selecting center positions of the extracted diffraction images corresponding to the pixel positions and correcting the center positions;
    creating an image set having diffraction information in which the center positions of the diffraction images respectively corresponding to the pixel positions have been corrected and aligned;
    selecting only innermost portions of the diffraction images of the created image set which correspond to the successive pixel positions; and
    reproducing STEM images from the diffraction images, thus obtaining a confocal STEM image.

2. A system for obtaining a confocal STEM image, comprising:
    a detector for detecting a diffraction image signal emanating from a sample when it is scanned in two dimensions with an electron beam;
    a memory for storing image data obtained by converting the signal detected by the detector into digital data; and
    arithmetic and control means connected with the detector and with the memory, controlling the detector, reading images from the memory, and performing given computational processing;
    wherein said arithmetic and control means extracts diffraction images respectively corresponding to successive pixel positions from the images stored in the memory, selects and corrects center positions of the extracted diffraction images corresponding to the pixel positions, creates an image set having diffraction information in which the center positions of the diffraction images have been corrected and aligned, selects only innermost portions of the diffraction images of the created image set, and reproduces STEM images from the diffraction images, thus obtaining a confocal STEM image.

* * * * *